(12) United States Patent
Harris et al.

(10) Patent No.: US 9,752,117 B2
(45) Date of Patent: Sep. 5, 2017

(54) HYBRID TISSUE SCAFFOLD FOR TISSUE ENGINEERING

(71) Applicant: Southwest Research Institute, San Antonio, TX (US)

(72) Inventors: Jeffrey N. Harris, San Antonio, TX (US); Jian Ling, Spring Branch, TX (US); Xingguo Cheng, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 14/467,879

(22) Filed: Aug. 25, 2014

(65) Prior Publication Data

US 2015/0050736 A1  Feb. 19, 2015

Related U.S. Application Data

(62) Division of application No. 13/712,583, filed on Dec. 12, 2012, now Pat. No. 8,815,594.

(51) Int. Cl.
*A61L 27/26* (2006.01)
*C12N 5/00* (2006.01)
*A61L 27/18* (2006.01)
*A61L 27/24* (2006.01)
(Continued)

(52) U.S. Cl.
CPC ............ *C12N 5/0068* (2013.01); *A61L 27/18* (2013.01); *A61L 27/24* (2013.01); *A61L 27/26* (2013.01); *A61L 27/38* (2013.01); *A61L 27/56* (2013.01); *A61L 2400/06* (2013.01); *C12N 2533/30* (2013.01); *C12N 2533/50* (2013.01); *C12N 2533/54* (2013.01); *C12N 2533/56* (2013.01); *C12N 2535/00* (2013.01)

(58) Field of Classification Search
CPC .......... A61L 27/24; A61L 27/26; A61L 27/56; A61L 27/38; C12N 2533/54; C12N 2533/56; C12N 2535/00; C12N 2533/50; C12N 2533/30
See application file for complete search history.

(56) References Cited

U.S. PATENT DOCUMENTS 8,815,594 B2  8/2014  Harris et al.
9,044,530 B2  6/2015  Ling et al.
9,456,893 B2  10/2016  Ling
(Continued)

OTHER PUBLICATIONS

Jiao et al., Fabrication and characterization of PLLA-chitosan hybrid scaffolds with improved cell compatibility. Journal of Biomedical Materials Research Part A, vol. 80A, No. 4 (online Oct. 20, 2006) pp. 820-825.*
(Continued)

*Primary Examiner* — Kara Johnson
(74) *Attorney, Agent, or Firm* — Grossman, Tucker et al.

(57) ABSTRACT

A hybrid tissue scaffold is provided which comprises a porous primary scaffold having a plurality of pores and a porous secondary scaffold having a plurality of pores, wherein the secondary scaffold resides in the pores of the primary scaffold to provide a hybrid scaffold. The pores of the porous primary scaffold may have a pore size in a range of 0.50 mm to 5.0 mm, and the pores of the porous secondary scaffold may have a pore size in a range of 50 μm to 600 μm. The primary scaffold may provide 5% to 30% of a volume of the hybrid scaffold.

13 Claims, 4 Drawing Sheets

(51) Int. Cl.
A61L 27/38 (2006.01)
A61L 27/56 (2006.01)

(56) References Cited

U.S. PATENT DOCUMENTS

| | | |
|---|---|---|
| 2008/0025956 A1 | 1/2008 | Yoder et al. |
| 2010/0168872 A1 | 7/2010 | Brown et al. |
| 2010/0279268 A1 | 11/2010 | Neumann et al. |
| 2011/0014597 A1 | 1/2011 | Frerich |
| 2011/0033927 A1 | 2/2011 | Rolle et al. |
| 2013/0030548 A1 | 1/2013 | Ling |
| 2014/0161841 A1 | 6/2014 | Harris et al. |
| 2014/0170117 A1 | 6/2014 | Ling et al. |

OTHER PUBLICATIONS

Wang et al., A hybrid scaffold of poly(lactide-co-glycolide) sponge filled with fibrin gel for cartilage tissue engineering. Chinese Journal of Polymer Science. vol. 29, No. 2 (Mar. 2011) pp. 233-240.*
Yamauchi, Kiyoshi et al., "Preparation of Collagen/Calcium Phosphate Multilayer Sheet Using Enzymatic Mineralization", Elsevier Ltd., Biomaterials, 2004, 5481-5489, References present in parent U.S. Appl. No. 13/712,583.
Yu, D, et al, "Bladder Wall Grafting in Rats Using Salt-modified and Collagen-coated Polycaprolactone Scaffolds Preliminary Report", International Journal of Urology (2007), vol. 14, pp. 939-944.
US Office Action issued in U.S. Appl. No. 13/720,543, mail date Aug. 13, 2013 (14 pgs).
US Office Action issued in U.S. Appl. No. 13/712,583, mail date Oct. 23, 2013 (12 pgs).
US Office Action issued in U.S. Appl. No. 13/720,543, mail date Apr. 8, 2014 (12 pgs).
US Office Action issued in U.S. Appl. No. 13/194,348, mail date Jul. 24, 2014 (13 pgs).
US Office Action issued in U.S. Appl. No. 13/720,543, mail date Sep. 23, 2014 (11 pgs).
US Office Action issued in U.S. Appl. No. 13/194,348, mail date Oct. 28, 2014 (15 pgs).
Antebi, et al "Biomimetic Collagen-Hydroxyapaptite Composite Fabricated Vla A Novel Perfusion—Flow Mineralization Technique"; Tissue engineering Part C, vol. 19, No. 7 (online ahead of editing Nov. 16, 2012) pp. 487-496.
Auger, et al., "Tissue-engineered skin substitutes: from in vitro constructs to in vivo applications," Biotechnol. Appl. Biochem., 39. (2004) pp. 263-275.
Badylak, et al, "Extracellular Matrix As a Biological Scaffold Material: Structure and Function"; ScienceDirect, Acta Biomaterialia, vol. 5, 2009, pp. 1-13.
Baht et al., "Bone Sialoprotein-collagen Interaction Promotes Hydroxyapaptite Nucleation", Matrix Biology, vol. 27 (2008) pp. 600-608.
Cartmell, et al; "Effects of Medium Perfusion Rate on Cell-Seeded Three-Dimensional Bone Constructs In Vitro"; Tissue Engineering, vol. 9, No. 6 (2003), pp. 1197-1203.
Cannillo, et al, "Fabrication of 45S5 Bioactive Glass-Polycaprolactone Composite Scaffolds"; 17th International Conference on Composite Materials (ICCM-17), Edinburgh (UK), Jul. 27-31, 2009 (downloaded Jul. 19, 2012 http://www.iccm-central.org/Proceedings/ICCM17proceedings/Themes/Applications/BIOMEDICAL%20APPLICATIONS/B1.5A%20Cannillo.pdf).
Chen, et al "Tissue Engineering of Cartilage Using A Hybrid Scaffold of Synthetic Polymer and Collagen." Tissue Engineering, vol. 10, No. 3/4 (2004) pp. 323-330.
Clarke, Bart , "Normal Bone Anatomy and Physiology", Clinical Journal of the American Society of Nephrology, vol. 3, 2008, S131-S139.
Colfen, Helmut , "A Crystal-Clear View", Nature Materials, News & Views; vol. 9, , Dec. 2010, 2010, 960-961.

Colton, "Implantable biohybrid artificial organs," Cell Transplant, vol. 4, No. 4. (1995) pp. 415-436.
Du, C. et al., "Formation of Calcium Phosphate/Collagen Composites Through Mineralization of Collagen Matrix", John Wiley & Sons, Inc.,, 2000, 518-527.
Fizgerald, "Collagen in wound healing: are we onto something new or just repeating the past?" The Foot and Ankle Online Journal, 2(9):3 (2009).
Gower, Laurie B. , "Biomimetic Model Systems for Investigating The Amorphous Precursor Pathway and Its Role in Biomineralization", 2008 American Chemical Society, Chem, Rev 2008, 108, 2008, 4551-4627.
Hirschi, et al., "PDGF, TGF-beta, and heterotypic cell-cell interactions mediate endothelial cell-induced recruitment of 10T1/2 cells and their differentiation to a smooth muscle fate," J Cell Biol, 141(3), (1998) pp. 805-814.
Hokugo, et al "Preparation of Hybrid Scaffold From Fibrin and Biodegradable Polymer Fiber", Biomaterials, vol. 27 (2006), pp. 61-67.
Huang, Zhi et al., "A Bone-like Nano-hydroxyapatite/collagen Loaded Injectable Scaffold", IOP Publishing, Biomedical Materials, Biomed Mater, 4, 2009, 1-7.
Karperien, et al; "Morphogenesis, Generation of Tissue in the Embryo"; Elsevier/Academic Press, Tissue Engineering, Senior Editor C.vanBlitterswijk; 2008 San Diego, CA, Book Publication Info and pp. 58-62.
Kikuchi, Masanori et al., "Self-organization Mechanism in a Bone-like Hydroxyapatite/collagen Nanocomposite Synthesized In Vitro and Its Biological Reaction In Vivo", Elsevier, Biomaterials 22 (2001), 2001, 1705-1711.
Kumar, et al., "Plastic surgery challenges in war wound," Advanced in Wound Care, 1, (2010) pp. 65-70.
Lantz, et al., "Small intestinal submucosa as a vascular graft: a review," J. Invest. Surg., 6(3), (1993) pp. 297-310.
Lee et al, "Designed Hybrid Scaffolds Consisting of Polycaprolactone Microstrands and Electrospun Collagen-Nanofibers for Bone Tissue Regeneration"; Journal of Biomedical Materials Research, Applied Biomaterials/ vol. 97B, Issue 2, (online 3-7-11—pp. 263-270).
Lees, Sidney et al., "A Study of Some Properties of Mineralized Turkey Leg Tendon", 1992 Gordon and Breach Science Publishers S.A.; Connective Tissue Research 1992, vol. 28, 1992, 263-287.
Liao et al, "Fabricaiton of Porous Biodegradable Polymer Scaffolds Using A Solvent Merging/Particulate Leaching Method.", Journal of Biomedical Materials Research, vol. 59, No. 4 (2001), pp. 676-681.
Lickorish, David , "Collagen-hydroxyapatite Composite Prepared by Biomimetic Process", Wiley Periodicals, Inc., J. Biomed Mater Res, 2003, 19-27.
Lockmic, et al., "An arteriovenous loop in a protected space generates a permanent, tightly vascular, tissue-engieered construct," FASEB, 21(2). (2007) pp. 511-522.
Luo, et al., "A multi-step method for preparation of porcine small intestinal submucosa (SIS)," Biomaterials, 32, (2011) pp. 706-713.
Markowicz, et al., "Enhancing the vascularization of three-dimensional scaffolds: new strategies in tissue regeneration and tissue engineering," Topics in Tissue Engineering, vol. 2, Chapter 6, \Eds. Ashammakhi N Reis RL.—2005 (15 pages).
Mikos, et al, "Preparation and Characterization of Poly(L-lactic acid)foams". Polymer, vol. 35, No. 5 (1994) pp. 1068-1077.
Moon, et al., "Vascularization of engineered tissues: approaches to promote angiogenesis in biomaterials," Current Topics in Medicinal Chemistry, 8(4), (2008) pp. 300-310.
Nillesen, et al., "Increased angiogenesis and blood vessel maturation in acellular collagen-heparin scaffolds containing both FGF2 and VEGF," Biomaterials, 28, (2007) pp. 1123-1131.
Olszta, Matthew J. et al., "Bone Structure and Formation: A New Perspective", Elsevier, Science Direct; Reports: A Review Journal, Materials Science and Engineering, R 58, 2007, 77-116.
Ozawa, Hidehiro et al., "Current Concepts of Bone Biomineralization", J. Oral Bioscience, 50(1), 2008, 1-14.
Paige, et al., "Engineering new tissue: formation of neocartilage," Tissue Eng., 1, (1995) pp. 97-106.

(56) References Cited

OTHER PUBLICATIONS

Park, et al., "Tissue engineering of urinary organ," Yonsei Med. J., 41, (2000) pp. 780-788.
Pek, Y.S. et al., "Porous Collagen-apatite Nanocomposite Foams As Bone Regeneration Scaffolds", Elsevier Biomaterials 29, 2008, 4300-4305.
Praetorius, et al; "Bending the MDCK Cell Primary Cilium Increases Intracellular Calcium"; Journal of Membrane Biology, vol. 184, 2001, pp. 71-79.
Prosecka, E. et al., "Optimized Conditions for Mesenchymal Stem Cells to Differentiate Into Osteoblasts on a Collagen/hydroxyapatite Matrix", Wiley Periodicals, Inc., Society for Biomaterials, J. Biomed Mater Res Part A 2011:99A, 2011, 307-315.
Raghavan, et al., "Physical characteristics of small intestinal submucosa scaffolds are location dependent," J. Biomed. Mater. Rec. A, 73, (2005) p. 90-96.
Ratcliffe, "A Tissue engineering of vascular grafts," Matrix Biol., 19, (2000) pp. 353-357.
Rodrigues, et al, "Characterization of a Bovine Collagen-Hydroxyapatite Composite Scaffold for Bone Tissue Engineering", Biomaterials, vol. 24, pp. 4987-4997 (2003).
Roeder, et al., "Compliance, elastic modulus, and burst pressure of small-intesine submucosa (SIS), small-diameter vascular grafts," J. Biomed Mater Res, 45.—(1999) p. 65-70.
Sakiyama-Elbert, et al., "Development of fibrin derivatives for controlled release of heparin-binding growth factors," J. Control. Release, 65, (2000) pp. 389-402.
Sikavitsas, et al "Mineralized Matrix Deposition by Marrow Stromal Osteoblasts in 3D Perfusion Culture Increases With Increasing Fluid Shear Forces."; Proceedings of The National Academy of Sciences, vol. 100, No. 25 (Dec. 9, 2003) pp. 14683-14688.
Thula, Taili T. et al., "In Vitro Mineralization of Dense Collagen Substrates: A Biomimetic Approach Toward The Development of Bone-graft Materials", Elsevier, Science Direct; Acta Biomaterialia, Inc. 7, 2011, 3158-3169.
Tsigkou, et al., "Engineered vascularized bone grafts," PNAS, 107(8), (2010) pp. 3311-3316.
Viguet-Carrin, S. et al., "The Role of Collagen in Bone Strength", Osteoporos International (2006) 17, Dec. 9, 2005, 319-336.
Wang, et al., "Osteogenesis and angiogenesis of tissue engineered bone construct by prevascularized β-tricalcium phosphate scaffold and mensenchymal stem cells," Biomaterials, 31, (2010) pp. 9452-9461.
Chen, et al; "Extracellular Matrix Made by Bone Marrow Cells Facilitates Expansion of Marrow-Derived Mesenchymal Progenitor Cells and Prevents Their Differentiation Into Osteoblasts"; Journal of Bone and Mineral research, vol. 22, No. 12, 2007 pp. 1943-1956.
Kashfi, et al, "A Review of Various Techniques of Orthotopic Liver Transplantation in the Rat"; Transplantation Proceedings, vol. 37, 2005, pp. 185-188.
Lai, et al; "Reconstitution of Marrow-Derived Extracellular Matrix Ex Vivo: A Robust Culture system for Expanding Large-Scale Highly Functional Human Mesenchymal Stem Cells"; Stem Cells and Development, vol. 19, No. 7, 2010, pp. 1095-1108.
Lange, et al, "Liver-Specific Gene Expression in Mesenchymal Stem Cells is Induced by Liver Cells"; World Journal of Gastroenterology, 2005, vol. 11, No. 29; pp. 4497-4504.
Linke, et al, "Engineered Liver-Like Tissue on a Capillarized Matrix for Applied Research"; Tissue Engineering, vol. 13, No. 11, 2007, pp. 2699-2707.
Slaughter, et al, "Hydrogels in Regenerative Medicine"; Advanced Materials 2009, vol. 21, pp. 3307-3329.
US Office Action issued in U.S. Appl. No. 13/194,348, mail date Mar. 31, 2015 (13 pgs).
US Office Action issued in U.S. Appl. No. 13/194,348, mail date Oct. 16, 2015 (15 pgs).
US Office Action issued in U.S. Appl. No. 14/728,336, mail date Oct. 21, 2016 (13 pgs).

\* cited by examiner

HYBRID TISSUE SCAFFOLD FOR TISSUE ENGINEERING

CROSS-REFERENCE TO RELATED APPLICATIONS

The present application is a divisional of co-pending U.S. patent application Ser. No. 13/712,583, filed on Dec. 12, 2012, the entire disclosure of which is incorporated herein by reference.

FIELD OF THE INVENTION

The present disclosure relates to a hybrid tissue scaffold for tissue implants and methods of for use thereof. The hybrid tissue scaffold includes a primary three-dimensional (base) scaffold which supports or otherwise carries a secondary three-dimensional scaffold, particularly within the pores thereof.

BACKGROUND

Engineered tissue implants require a tissue scaffold that is preferably made of similar materials to the tissue that will be replaced by the engineered tissue implant. This requires using biomaterials such as, but not limited to, collagen, fibrin, and glycosaminoglycans (GAGs). However, while these materials may provide the correct biomaterial environment, they lack the mechanical strength required to be implanted. Such forces may be generated from in situ forces, such as pressure from fluids passing through or by the implant. Further, the tissue implants need to be able to withstand the forces of being handled and surgically implanted by the surgeon. This is a common, long standing problem that has made designing a tissue engineering implant very difficult.

Many different techniques have been used to try to overcome the lack of mechanical strength in scaffolds, and the corresponding lack of strength in the implant. These include processing techniques such as crosslinking the materials. However, this typically does not create sufficient increased strength. In addition, the crosslinkers are usually cytotoxic, which adds the complexity of thoroughly rinsing the samples to remove excess crosslinker. Other techniques have copolymerized the biomaterials with a stiffer, usually synthesized, polymer. This greatly increases the cost of manufacturing the material and can be hard to fabricate the material into a scaffold. In addition, scaffolds have been developed from a relatively stiff synthesized polymer with pore sizes in the range of a few hundreds of microns in diameter, which have then been coated with a biomaterial. This technique can provide the strength required, but results in a mostly synthetic scaffold with minimal biomaterial that the cells cannot remodel. Once the biomaterials are degraded only the synthetic polymer remains.

SUMMARY

The present disclosure provides new structures and methods to improve the mechanical strength of a hybrid tissue scaffold of an engineered tissue implant. The disclosure provides a hybrid tissue scaffold comprising a primary three-dimensional (base) scaffold which supports or otherwise carries a secondary three-dimensional scaffold, particularly within the pores thereof. More particularly, the porous primary scaffold may have a pore size in a range of between and including 0.50 mm to 5.0 mm, while the secondary scaffold may have a relatively smaller pore size, such as in the range between and including 50 µm to 600 µm (microns).

The primary scaffold may be fabricated from a variety of polymer materials and have different pore geometries to achieve the desired strength for a given application. The primary scaffold provides a framework or skeleton into which the secondary scaffold can be introduced. In contrast to the primary scaffold, the secondary scaffold may particularly be formed of a natural biomaterial, such as a naturally occurring polymer. The naturally occurring polymer may be a protein (e.g. collagen, fibrin) or a carbohydrate (e.g. a polysaccharide such as chitosan, glycosaminoglycan).

The biomaterial, which may be in the form of a hydrogel, may be injected into the pores of the primary scaffold and reside therein. The biomaterial may be injected with or without seeding cells, and may be processed to provide a micro porous scaffold with designed pore size and geometries.

In the foregoing manner, the primary scaffold will only occupy a relatively smaller volume of the hybrid scaffold or engineered tissue implant, yet provide the needed strength of the implant for implantation while the biomaterial provides the appropriate environment for the seeding stem cells to proliferate.

The hybrid tissue scaffold or engineered tissue implant may accelerate the wound healing process since they are able to: 1) cover the wound site to keep the wound moist and to reduce the risk of infection; 2) reduce tissue regeneration time through the incorporation of functional tissue developed in vitro; and 3) provide a source of stem cells to the wound sites for tissue regeneration.

In certain embodiments, a hybrid tissue scaffold may comprise a porous primary scaffold having a plurality of pores, and a porous secondary scaffold having a plurality of pores, wherein the secondary scaffold resides in the pores of the primary scaffold to provide a hybrid scaffold. The pores of the porous primary scaffold may have a pore size in a range of 0.50 mm to 5.0 mm, and the pores of the porous secondary scaffold have a pore size in a range of 50 µm to 600 µm. The primary scaffold may provide 5% to 30% of a volume of the hybrid scaffold. In other embodiments, the pores of the porous primary scaffold may have a pore size in a range of 1 mm to 4 mm, and the pores of the porous secondary scaffold may have a pore size in a range of 100 µm to 500 µm.

In certain embodiments, the porous primary scaffold may be formed of a synthetic polymer, and the synthetic polymer may be biodegradable in a human body. The synthetic polymer may be polyester, and may particularly include polycaprolacone (PCL).

In certain embodiments, the secondary scaffold may be formed of a biomaterial which provides an environment to culture living cells therein and promote attachment, migration, proliferation, and/or vascularization of the cells. The biomaterial may be formed of a naturally occurring polymer. The naturally occurring polymer may be a protein (e.g. collagen, fibrin) and/or a carbohydrate. The secondary porous scaffold may be in the form of a hydrogel or porous scaffold.

In certain embodiments, a plurality of living cells may be seeded to at least one of the primary scaffold and the secondary scaffold. The cells may comprise at least one of endothelial, fibroblast and/or stem cells.

In certain embodiments, a method to provide a tissue scaffold comprises forming a hybrid scaffold comprising a porous primary scaffold having a plurality of pores and a porous secondary scaffold having a plurality of pores, wherein the secondary scaffold resides in the pores of the primary scaffold to provide the hybrid scaffold. The pores of the porous primary scaffold may have a pore size in a range of 0.50 mm to 5.0 mm, and the pores of the porous secondary scaffold may have a pore size in a range of 50 μm to 600 μm. The primary scaffold may provide 5% to 30% of a volume of the hybrid scaffold.

In certain embodiments, the method may further comprise forming the porous primary scaffold with the plurality of pores and introducing the porous secondary scaffold into the pores of the porous primary scaffold.

In certain embodiment, the method may further comprise injecting the porous secondary scaffold into the pores of the porous primary scaffold.

In certain embodiments, the porous secondary scaffold is in the form of a hydrogel, and the method may further comprise injecting the hydrogel into the pores of the porous primary scaffold.

In certain embodiments, forming the hybrid scaffold may be performed in situ during a surgical procedure on a human body.

In certain embodiments, the method may further comprise fitting the porous primary scaffold to a tissue treatment site of a human body before introducing the porous secondary scaffold into the pores of the porous primary scaffold.

FIGURES

The above-mentioned and other features of this disclosure, and the manner of attaining them, will become more apparent and better understood by reference to the following description of embodiments described herein taken in conjunction with the accompanying drawings, wherein.

DETAILED DESCRIPTION

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Figure 1:
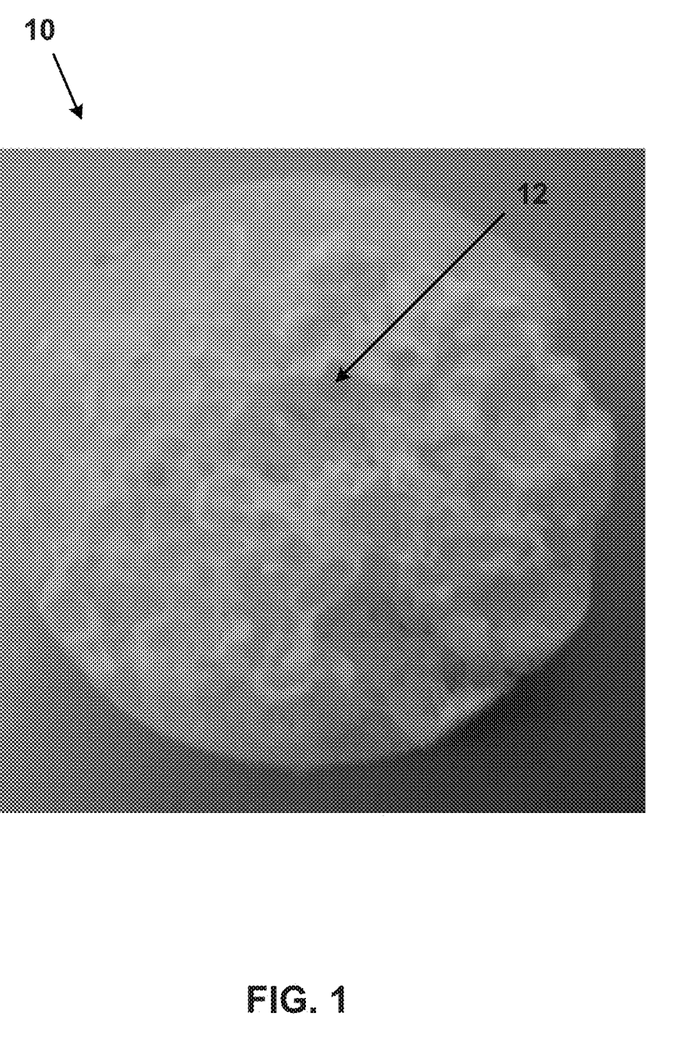
FIG. 1 is an image of a primary scaffold according to one embodiment of the present disclosure.

Referring now to figures, an exemplary primary scaffold according to the present invention is shown in FIG. 1 at reference character 10. The primary scaffold 10 provides a framework or skeleton into which a secondary scaffold may be introduced (e.g. injected or otherwise filled) into the plurality of pores 12 thereof. The pores of the primary scaffold 10 may have a pore size in a range of between and including 0.50 mm to 5.0 mm. More particularly, the pores of the primary scaffold 10 may preferably have a pore size in a range of between and including 1.0 mm to 4.0 mm. The primary scaffold 10 itself may have a porosity level in a range of between and including 50% to 99%.

The primary scaffold 10 of FIG. 1 may preferably be made of a biodegradable polymer such as a polyester polymer including polycaprolactone (PCL) or poly(lactic-co-glycolic acid) (PLGA). PCL reportedly has melting point of about 60° C. and a glass transition temperature of about −60° C. Reference to biodegradable may be understood herein as the ability to undergo enzymatic degradation or nonenzymatic hydroylysis and to provide non-toxic metabolites that may then be eliminated by the body. It is therefore contemplated herein that biodegradable polymers suitable for preparation of the primary scaffold 10 may also include polyurethane, poly (urethane urea), polyhydroxyalkanoates (PHAs), poly(l-lactic acid) (PLLA), polyanhydrides, polyfumerates, poly(n-isopropylacrylamide, or polypeptides.

The fabrication of the primary scaffold herein may proceed by at least two related methods. The first method may be generally understood as providing a solution of the biodegradable polymer (polyester) that is mixed with insoluble inorganic salt particulate wherein the salt has a size range of 0.50 to 5.0 mm. This is then followed by relatively rapid cooling where the rate of cooling is such that the polyester (PCL) will precipitate followed by evaporating the solvent before treatment with water to dissolve the salt and provide a pore size range of 0.50 mm-5.0 mm. Preferably, the rate of cooling is 1 degree Celsius per minute. Exemplary salts include NaCl, NaHCO$_3$, urea, and various sugars.

A preferred fabrication according to the first method noted above is to start with a 10% (w/w) PCL solution made by dissolving PCL in organic solvents, such as 65% (w/w) chloroform and methanol solution. The PCL solution was then mixed with a salt that was previously sieved to the range of 0.85 mm to 1.40 mm. The solution was then placed in a freezer at −20° C. to provide PCL precipitation. The samples were then placed in a fume hood to allow the solvents to evaporate. Next, the samples are placed in second solvent such as water to dissolve out the salt resulting in the formation of a porous PCL scaffold 10. As noted, such porous PCL scaffold has a pore size range of 0.50-5.0 mm. See again, FIG. 1.

A second related method to fabricate the primary scaffold 10 may proceed by mixing a salt in a size range of 0.50 mm-5.0 mm with biodegradable polymer particulate having a size less than or equal to 0.5 mm, or in the range of 0.5 mm to 5.0 mm. The biodegradable polymer (e.g. PCL) may then be heated at a temperature sufficient to sinter the PCL particles or treated with solvent to form a continuous phase of the PCL around the salt. Sintering may be understood as heating to a sufficient temperature to join the PCL particles and the treatment with solvent is also such that the particles are joined to form the identified continuous phase. The salt is such that it again will not dissolve or melt, as the salt may then again define the porosity to be achieved when the salt is ultimately removed from the continuous phase of biodegradable polymer (PCL). That is, the salt, present at a size of 0.50 mm to 5.0 mm, is dissolved to obtain the porous PCL scaffold 10. The pore size of the PCL scaffold may again be in the range of 0.50 mm to 5.0 mm, and preferably in the range of 1.0 mm to 4.0 mm (due to use of correspondingly lower salt size). The PCL scaffold 10 then once again serves as the skeleton of the hybrid tissue scaffold/engineered tissue implant disclosed herein, and provides a framework for the hybrid tissue scaffold/implant to withstand the forces during in vivo implantations. As noted above, the PCL scaffold is configured such that it will amount to 5.0% to 30.0% of the hybrid scaffold volume, more preferably in the range of 10.0% to 20.0% by volume, and more preferably, 14.0% to 16.0% by volume.

Figure 2:
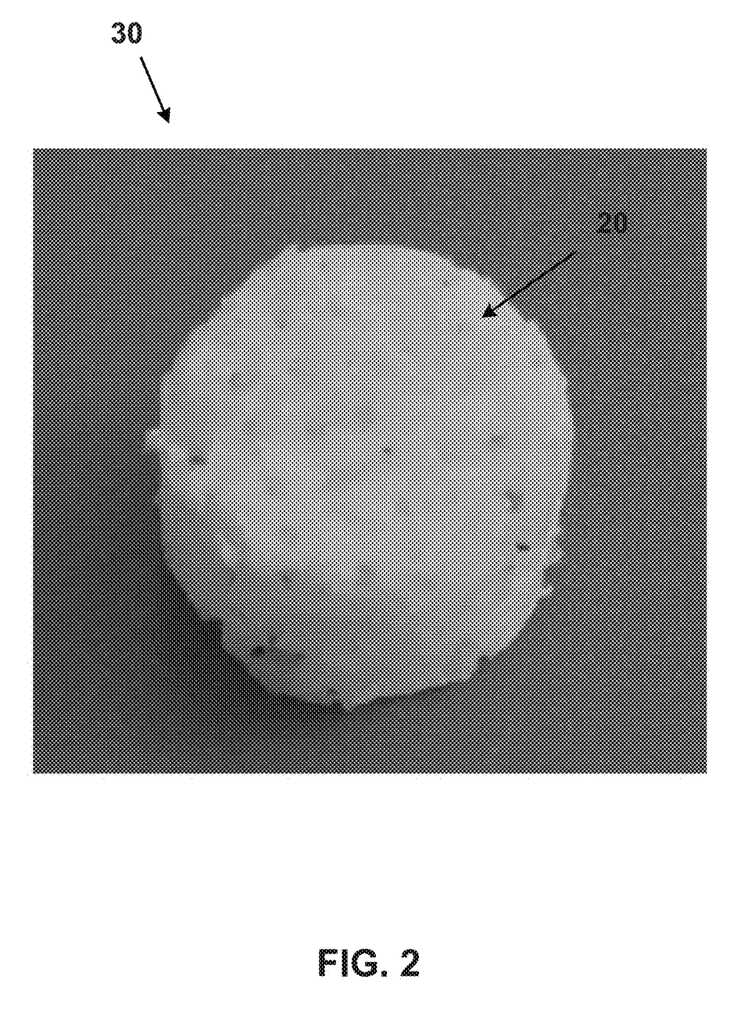
FIG. 2 is an image of a hybrid scaffold according to one embodiment of the present disclosure which makes use of the primary scaffold of FIG. 1.

Once the primary scaffold 10 is fabricated, a porous secondary scaffold 20 may be introduced into the pores 12 of the primary scaffold 10. Referring now to FIG. 2, a secondary scaffold 20 is shown residing in, such as by being injected into the pores in the primary scaffold 10. The secondary scaffold 20 is preferably formed of a biomaterial (any matter, surface, or construct that interacts with biological systems of a human body) and which provides an environment to culture living seeded cells and promote cell attachment, migration, proliferation, and/or vascularization. To facilitate injection and biological interaction, the secondary scaffold 20 may particularly be in the form of a hydrogel. A hydrogel herein may be understood as a network of polymer chains that are hydrophilic in which water is the dispersion medium.

The pores of the secondary scaffold 20 may have a pore size in a range of between and including 50 μm to 600 μm. More particularly, the pores of the secondary scaffold 20 may have a pore size in the range of 200 μm to 500 μm. The secondary scaffold 20 may have a porosity level in a range of between and including 50% to 99% by volume.

The biomaterial may be formed of a naturally occurring polymer which is a protein (e.g. collagen, fibrin) and/or a carbohydrate e.g. a polysaccharide such as chitosan, glycosaminoglycan. FIG. 2 shows a secondary scaffold 20 of collagen introduced to and residing in the pores 12 of primary scaffold 10, the combination of which provides a PCL-collagen hybrid scaffold 30.

Figure 3:
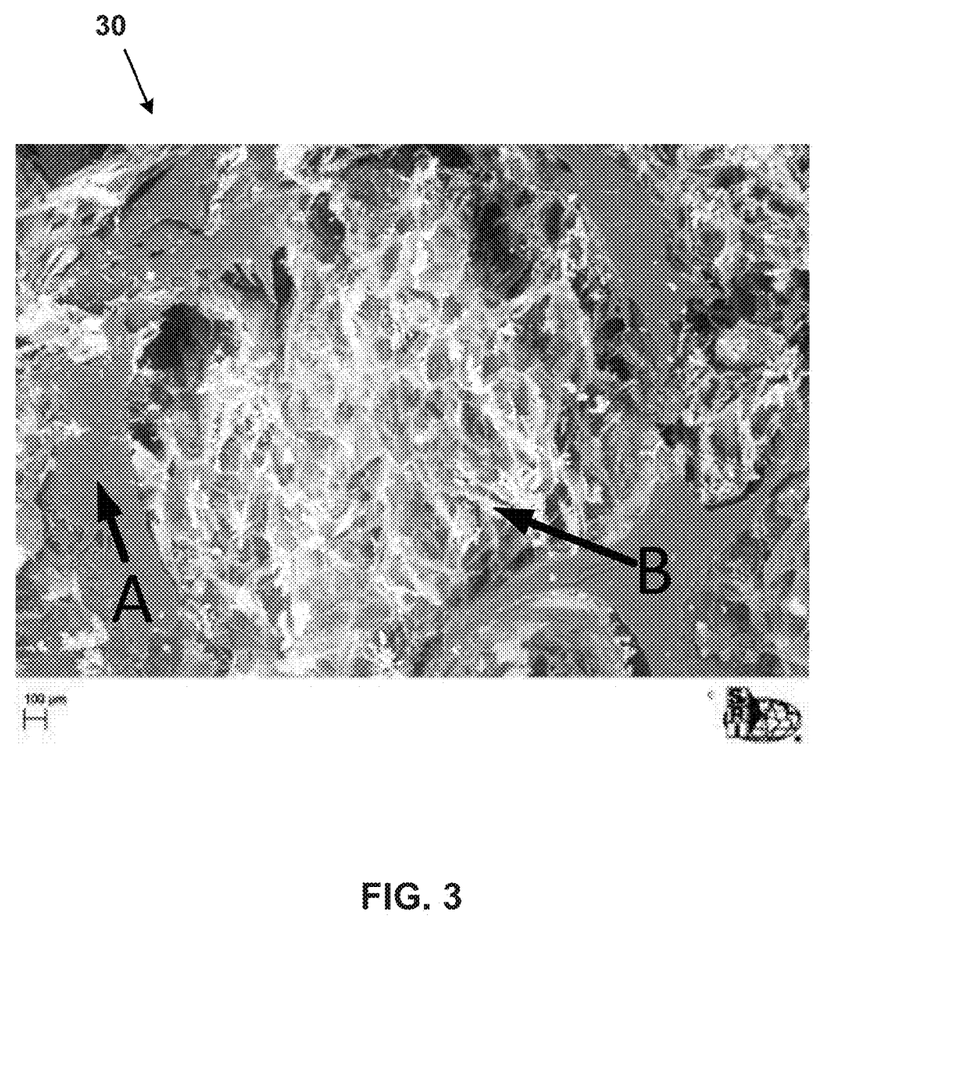
FIG. 3 is an image of the microstructure of PCL-collagen hybrid scaffold of FIG. 2 imaged by an environmental electron scanning microscope (ESEM)

FIG. 3 shows the microstructure of PCL-collagen hybrid scaffold 30 imaged by an environmental electron scanning microscope (ESEM). Arrow A illustrates the location of the PCL primary scaffold 10, while arrow B illustrates the location of the collagen secondary scaffold 30. The collagen scaffold 30 has interconnected pores with an average diameter of 250 μm within the collagen material and the porosity was about 70%.

As noted, the primary scaffold herein may provide 5.0% to 30.0% of the hybrid scaffold volume. In this manner, the primary scaffold 10 may provide the needed strength of the hybrid scaffold/implant for implantation while the filler biomaterial of the secondary scaffold 20 provides the needed environment for seeded stem cells to proliferate. While the primary PCL scaffold 10 therefore represents only a portion of the volume of the PCL-collagen hybrid scaffold 30, the PCL scaffold 10 may now unexpectedly enhance the mechanical stiffness of the PCL-collagen hybrid scaffold 30 while preserving the ability of the scaffold to provide the correct material environment for cell proliferation.

More specifically, it has been found that the PCL-collagen hybrid scaffold 30 exhibits a Young's modulus in the range of 0.1 MPA to 100 GPa, more preferably, 1.80 to 2.2 MPa. Young's modulus of the hybrid scaffold is measured by unconfined compression. By comparison, it has been found that scaffolds which rely upon only crosslinked collagen (where crosslinking was employed to increase the modulus value and overcome the problem of relatively poor mechanical strength), indicate Young's modulus value of about 23 kPa. As can therefore be appreciated, the present hybrid scaffold provides magnitudes of order improvement in mechanical property characteristics, such as Young's modulus, thereby achieving the goal of strength improvement in the hybrid scaffold without the need to crosslink and/or extraction of chemical crosslinking agents. In addition, the present hybrid skeleton approach allows for mechanical property improvement without the need to crosslink the biomaterial. A scaffold is nonetheless produced that withstands loading forces during implantation where it may be press-fit into a selected location.

Figure 4:
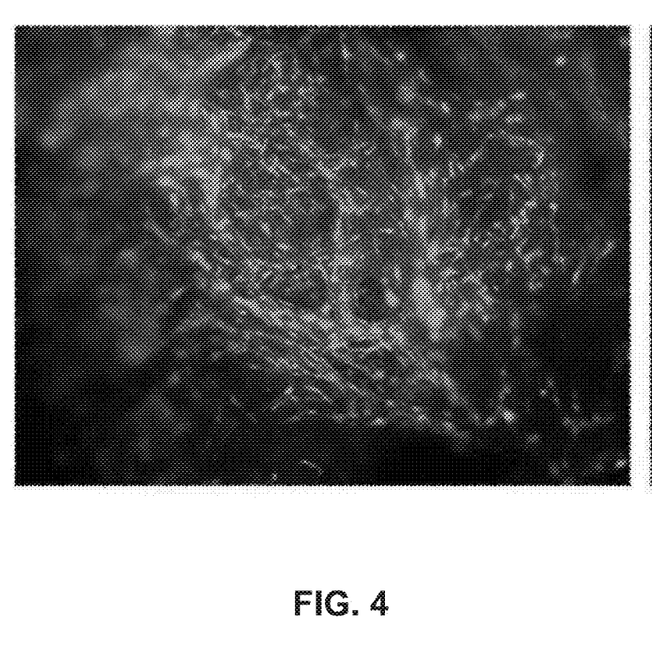
FIG. 4 is an image of live/dead staining of cells within the collagen of a PCL-collagen hybrid scaffold.
Figure 5:
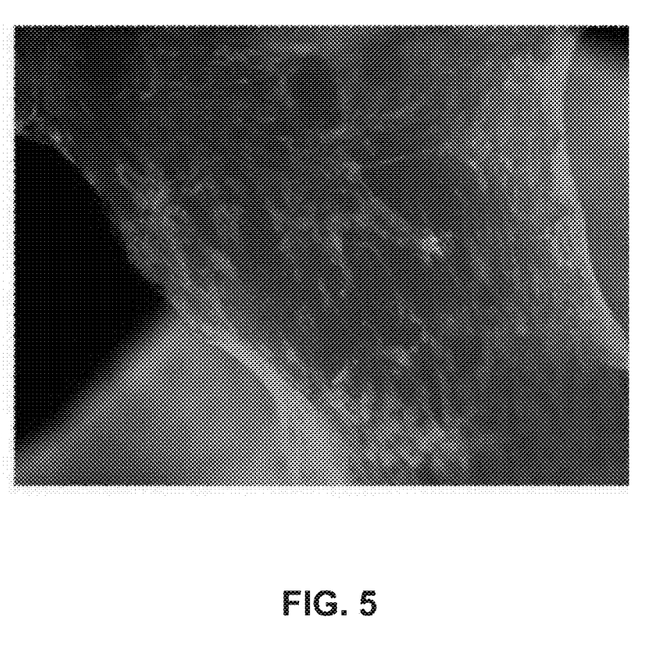
FIG. 5 is an image of live/dead staining of cells on the surface of the polycaprolactone of a PCL-collagen hybrid scaffold.

Additional embodiments of the hybrid scaffold 30 include using fibrin as the secondary scaffold 20 to be introduced into the pores of the primary scaffold 10 instead of collagen. Both the PCL-collagen hybrid scaffold 30 and the PCL-fibrin hybrid scaffold 30 have been found to successfully house seeded cells, such as stem, endothelial, and fibroblast cells, and allow them to create extracellular matrix and remodel the material in an in vitro culture. FIG. 4 shows live/dead staining of cells within the collagen of the PCL-collagen hybrid scaffold 30. FIG. 5 shows live/dead staining of cells on the surface of the polycaprolactone of the PCL-collagen hybrid scaffold 30.

Thus, the foregoing technique may also provide enhanced versatility of applications. The pores of the primary scaffold may be injected or otherwise filled with the biomaterial and processed to form the hybrid tissue scaffold/engineered implant prior to use thereof. The hybrid tissue scaffold therefore relies only upon the presence of the primary scaffold of the indicated polymers and secondary scaffold material as disclosed herein and avoids dependence on the use of any other components (e.g. crosslinking agents in the secondary scaffold or the use of copolymer structure in the secondary scaffold biomaterial). The hybrid tissue scaffold also does not rely upon the presence of glass. Accordingly, the present disclosure provides transplantable hybrid tissue scaffolds/implants that can be vascularized or even predeveloped into functional tissue in vitro and then transplanted in vivo as engineered tissue substitute at a tissue treatment site. The hybrid tissue scaffold/engineered implant may be configured to connect with host blood vessels in vivo to supply oxygen and nutrition to cells thereof immediately after the implantation.

In addition, as alluded to above, the bare primary scaffold can be shapeable as to conform to the anatomical shape of a wound or other tissue treatment site (e.g. press fit and/or cut to fit) and then the biomaterial can be injected into the primary scaffold in situ in a minimally invasive procedure. The biomaterial is configured to integrate into surrounding host tissue to achieve wound healing. The hybrid tissue scaffold or engineered tissue implant may comprise a same or similar tissue type as the lost tissue at the tissue treatment site. The tissue scaffold construct/engineered tissue implant may be developed into functional tissue types such as muscle, bone, cartilage, and epithelial in vitro. Further, the hybrid tissue scaffold may be loaded with drugs or growth factors to better control the integration into the surrounding tissue.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

What is claimed is:

1. A hybrid tissue scaffold comprising:
a porous primary scaffold of biodegradable polymer having pores in a pore size range of 1.0 mm to 4.0 mm;
a porous secondary scaffold formed from a biomaterial injectable into the pores of the porous primary scaffold, the biomaterial comprising a hydrated hydrogel including living cells, wherein the secondary scaffold resides in the pores of the primary scaffold to provide a hybrid scaffold;
wherein the biomaterial provides an environment to culture the living cells and the biomaterial has a pore size range of 50 μm to 600 μm; and
wherein the primary scaffold provides 5% to 30% of a volume of the hybrid scaffold and said hybrid scaffold has a Young's modulus of 0.1 MPA to 100 GPa.

2. The tissue scaffold of claim 1 wherein:
the pores of the porous secondary scaffold have a pore size in a range of 200 μm to 500 μm.

3. The tissue scaffold of claim 1 wherein:
the porous primary biodegradable scaffold comprises a synthetic polymer.

4. The tissue scaffold of claim 3 wherein:
the synthetic polymer is a polyester.

5. The tissue scaffold of claim 1 wherein:
the biomaterial further comprises a naturally occurring polymer.

6. The tissue scaffold of claim 5 wherein:
the naturally occurring polymer is a protein.

7. The tissue scaffold of claim 6 wherein:
the protein is collagen.

8. The tissue scaffold of claim 6 wherein:
the protein is fibrin.

9. The tissue scaffold of claim 5 wherein:
the naturally occurring polymer is a carbohydrate.

10. The tissue scaffold of claim 1 wherein:
the cells comprise at least one of endothelial, fibroblast and stem cells.

11. The tissue scaffold of claim 1 wherein:
the biomaterial does not contain any crosslinking.

12. The tissue scaffold of claim 1 wherein:
the primary scaffold is provides 10.0% to 20.0% of the volume of the hybrid scaffold.

13. The tissue scaffold of claim 1 wherein:
the biomaterial has a porosity of 50% to 99% by volume.

* * * * *